US012510226B1

(12) United States Patent
Funk et al.

(10) Patent No.: US 12,510,226 B1
(45) Date of Patent: Dec. 30, 2025

(54) HOME ACCESSORIES WITH BACKLIT EFFECT

(71) Applicant: BeautyAvenues, LLC, Reynoldsburg, OH (US)

(72) Inventors: Tobias Funk, Columbus, OH (US); Anya Schmidt, Columbus, OH (US); Laura Lees, Blacklick, OH (US)

(73) Assignee: BeautyAvenues, LLC, Reynoldsburg, OH (US)

( * ) Notice: Subject to any disclaimer, the term of this patent is extended or adjusted under 35 U.S.C. 154(b) by 0 days.

(21) Appl. No.: 18/757,784

(22) Filed: Jun. 28, 2024

Related U.S. Application Data

(60) Provisional application No. 63/511,299, filed on Jun. 30, 2023.

(51) Int. Cl.

| | |
|---|---|
| ***F21V 3/06*** | (2018.01) |
| ***A61L 9/03*** | (2006.01) |
| ***F21S 8/00*** | (2006.01) |
| ***F21V 3/10*** | (2018.01) |
| ***F21V 35/00*** | (2006.01) |

(52) U.S. Cl.
CPC ................ *F21V 3/06* (2018.02); *A61L 9/037* (2013.01); *F21S 8/035* (2013.01); *F21V 3/10* (2018.02); *F21V 35/00* (2013.01); *A61L 2209/133* (2013.01)

(58) Field of Classification Search
CPC .... A61L 9/037; A61L 2209/133; F21S 8/035; F21V 3/049; F21V 35/00
See application file for complete search history.

(56) References Cited

U.S. PATENT DOCUMENTS

| | | | | |
|---|---|---|---|---|
| 4,017,729 | A * | 4/1977 | Frazier, Jr. .............. | F21V 13/10 431/291 |
| 6,236,807 | B1 | 5/2001 | Ruffolo et al. | |
| 7,277,626 | B2 | 10/2007 | Pesu et al. | |
| 7,932,482 | B2 | 4/2011 | Norwood et al. | |
| 8,301,019 | B2 | 10/2012 | Smith et al. | |
| 9,395,061 | B2 * | 7/2016 | Yang ....................... | F21S 6/001 |
| 10,260,706 | B2 * | 4/2019 | Wu ........................... | F21V 3/04 |
| D969,290 | S | 11/2022 | Guerin et al. | |
| D998,775 | S | 9/2023 | Guerin et al. | |

(Continued)

OTHER PUBLICATIONS

Pottery Barn, “Ghost Hologram Mirror,” accessed Aug. 7, 2024, available at https://www.potterybarn.com/products/ghost-hologram-mirror/.

(Continued)

*Primary Examiner* — Mariceli Santiago
(74) *Attorney, Agent, or Firm* — Andrus Intellectual Property Law, LLP

(57) ABSTRACT

An assembly comprises a light source configured to be selectively illuminated; an outer decorative element; and an inner decorative element between the light source and the outer decorative element. The outer decorative element comprises a transparent or translucent substrate that is coated with a metal coating. The inner decorative element is not visible through the outer decorative element when the light source is not illuminated. The inner decorative element is visible through the outer decorative element when the light source is illuminated.

20 Claims, 7 Drawing Sheets

(56) References Cited

U.S. PATENT DOCUMENTS

| | | | | |
|---|---|---|---|---|
| 2003/0064337 | A1* | 4/2003 | Pesu | F21V 35/00 431/291 |
| 2011/0027124 | A1 | 2/2011 | Albee et al. | |
| 2014/0268670 | A1* | 9/2014 | Yang | F21S 6/001 362/101 |
| 2014/0268804 | A1* | 9/2014 | Yang | F21S 8/035 362/311.06 |
| 2016/0015849 | A1 | 1/2016 | Lagace et al. | |
| 2016/0193377 | A1 | 7/2016 | Lagace et al. | |
| 2021/0015955 | A1 | 1/2021 | Harrell et al. | |
| 2023/0226242 | A1 | 7/2023 | Harrell et al. | |

OTHER PUBLICATIONS

Funk, Tobias et al., "Fragrance Dispenser With Decorative Cover Assembly," U.S. Appl. No. 18/106,762, filed Feb. 7, 2023 (specification, claims, and drawings only).

* cited by examiner

HOME ACCESSORIES WITH BACKLIT EFFECT

CROSS-REFERENCE TO RELATED APPLICATION

The present application claims the benefit of U.S. Provisional Application No. 63/511,299, filed Jun. 30, 2023, which is hereby incorporated by reference herein in its entirety.

FIELD

The present disclosure relates to decorative home accessories, such as but not limited to, candle holders, table-top objects, home fragrance dispensers, and the like.

BACKGROUND

U.S. Pat. No. 6,236,807 discloses a vapor emanation system including a plastic housing having a socket portion and an electric plug portion. A decorative miniaturize container containing liquid to be evaporated by heat, has a body for storing the liquid and a neck connected to the body for engaging the socket portion of the housing for supporting the container on the housing. The neck has a passage there through and a retaining ring is fixed in the passage. A hole extends through the ring. A wick having an upper portion extending through the hole of the retaining ring also has a lower portion extending down into the body of the container for absorbing liquid from the container and for moving the liquid into the upper portion of the wick by capillary action. A tangential electric heater in the housing heats the upper portion of the wick above the neck to evaporate liquid from the wick. A retaining pin extending through the wick below the neck, extends radially beyond the wick by an amount which precludes upward extraction of the wick from the retaining ring to prevent a child from removing the wick and being exposed to the liquid.

U.S. Pat. No. 7,277,626 discloses an apparatus and method that combines a nightlight and an air freshener in a single device. The apparatus includes circuitry where a single resistor heats a heating block that heats and releases a volatile aromatic. The resistor also limits the current that passes through one or more light emitting diodes. The aromatic may be liquid scented oil held by a container. The container may also include a protruding wick that is heated by the heating block to facilitate oil evaporation. The light emitting diodes illuminate the housing and a decorative shield. The diodes may also illuminate fiber optic cables. The apparatus receives alternating current from a standard wall outlet. The circuitry utilized by the device ensures that the resistor is continuously powered during both half-cycles of the alternating current resulting in optimal heating of the aromatic.

U.S. Pat. No. 8,301,019 discloses a fragrance emanation system including a container for holding preferably a fragranced liquid or gel, a housing for holding the container, and a wick. The housing contains a socket for attaching to the container, a cavity for receiving the container and a door for enclosing the container. One end of the wick protrudes from the container. An electrical circuit is included having a heater for heating the protruding end of the wick and electrical connectors coupled to the circuit to receive current from a power source to provide the current to the heater. The heater heats and evaporates the liquid within the wick, thereby accelerating the emission of vapors from the evaporated liquid. The door includes a window, a bottom and a mechanism for holding the door closed to assist in holding the container in engagement with the socket.

U.S. Patent Application Publication No. 2021/0015955 discloses a fragrance dispenser comprising a housing having a socket portion and defining a receptacle configured to receive a bottle having a fragrance-producing liquid therein and a wick extending therefrom. A heater can be disposed proximate to the receptacle so that, when the bottle is received within the receptacle, the heater is disposed proximate to the wick. A controller can be configured to deliver electrical voltage (e.g., pulse-width-modulated voltage) to the heater. A user input device can be in communication with the controller.

U.S. patent application Ser. No. 18/106,762, filed Feb. 7, 2023, discloses a fragrance dispenser including a housing having a socket portion defining a receptacle for receiving a bottle of fragrance therein. A decorative cover assembly is coupled to the housing and conceals at least part of the socket portion. The decorative cover assembly comprises an outer cover and a light source positioned between the housing and the outer cover. Various illuminated effects are created by the light source and cover assembly, including a neon-like effect, a twinkle effect, and a projected image effect.

The above patents and publications are provided by way of background information and are hereby incorporated by reference herein in their entireties.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

According to one example of the present disclosure, an assembly comprises a light source configured to be selectively illuminated; an outer decorative element; and an inner decorative element between the light source and the outer decorative element. The outer decorative element comprises a transparent or translucent substrate that is coated with a metal coating.

According to some aspects, the metal coating is reflective.

According to some aspects, the metal coating is configured to reflect external light outwardly away from the outer decorative element.

According to some aspects, the inner decorative element is not visible through the outer decorative element when the light source is not illuminated.

According to some aspects, the inner decorative element is visible through the outer decorative element when the light source is illuminated.

According to some aspects, the inner decorative element is not visible through the outer decorative element when the light source is not illuminated, and the inner decorative element is visible through the outer decorative element when the light source is illuminated.

According to some aspects, the transparent or translucent substrate is plastic.

According to another example of the present disclosure, an assembly comprises a light source configured to be selectively illuminated; an outer decorative element; and an inner decorative element between the light source and the outer decorative element. The inner decorative element is not visible through the outer decorative element when the light source is not illuminated. The inner decorative element is visible through the outer decorative element when the light source is illuminated.

According to some aspects of either example, the outer decorative element, the inner decorative element, and the light source are coupled to a base that is in turn configured to be coupled to a power source. The light source is configured to be electrically connected to the power source so as to illuminate the light source.

According to some aspects of either example, the assembly is a plug-in fragrance dispenser. According to some aspects, a base is configured to support the outer decorative element, the inner decorative element, and the light source. A plug is coupled to the base and is configured to connect the light source to a power source to selectively illuminate the light source. A heater is supported by the base and is configured to emit heat when selectively connected to the power source via the plug. The base is configured to hold a bottle comprising a fragrant liquid therein in a manner such that a wick extending from the bottle is located adjacent the heater. The outer decorative element is configured to at least partially hide the base from view when the assembly is viewed from a front side thereof.

According to some aspects of either example, the assembly is a candle holder.

According to some aspects of either example, the inner decorative element is translucent.

According to some aspects of either example, the inner decorative element is opaque and comprises one or more apertures therein.

BRIEF DESCRIPTION OF THE DRAWINGS

The present disclosure is described with reference to the following Figures. The same numbers are used throughout the Figures to reference like features and like components.

DETAILED DESCRIPTION

Figure 1:
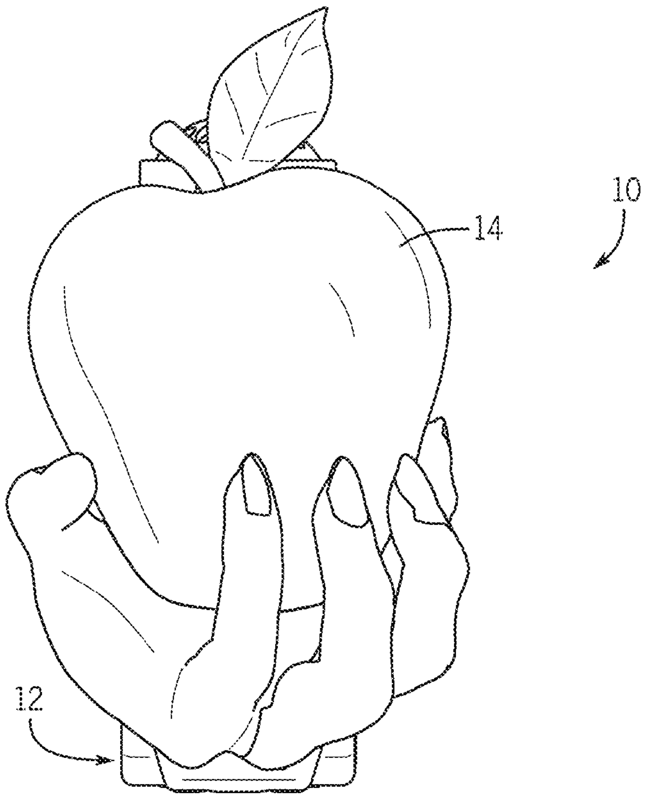
FIG. 1 is a front view of a first example of an assembly according to the present disclosure.
Figure 2:
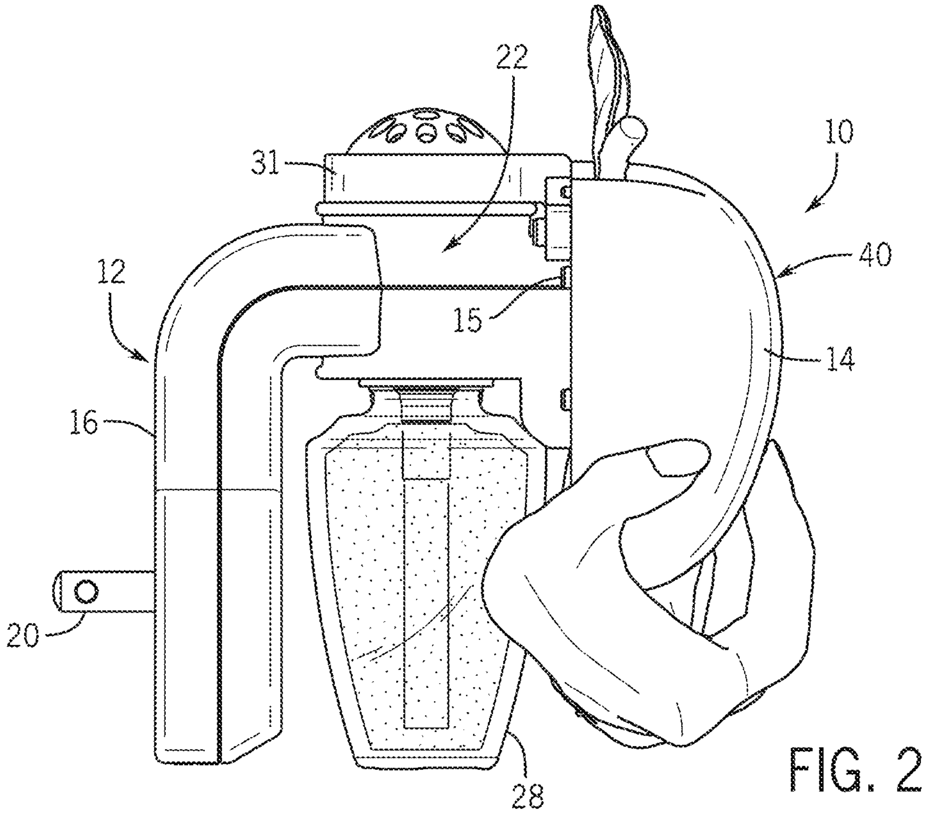
FIG. 2 is a side view thereof.
Figure 3:
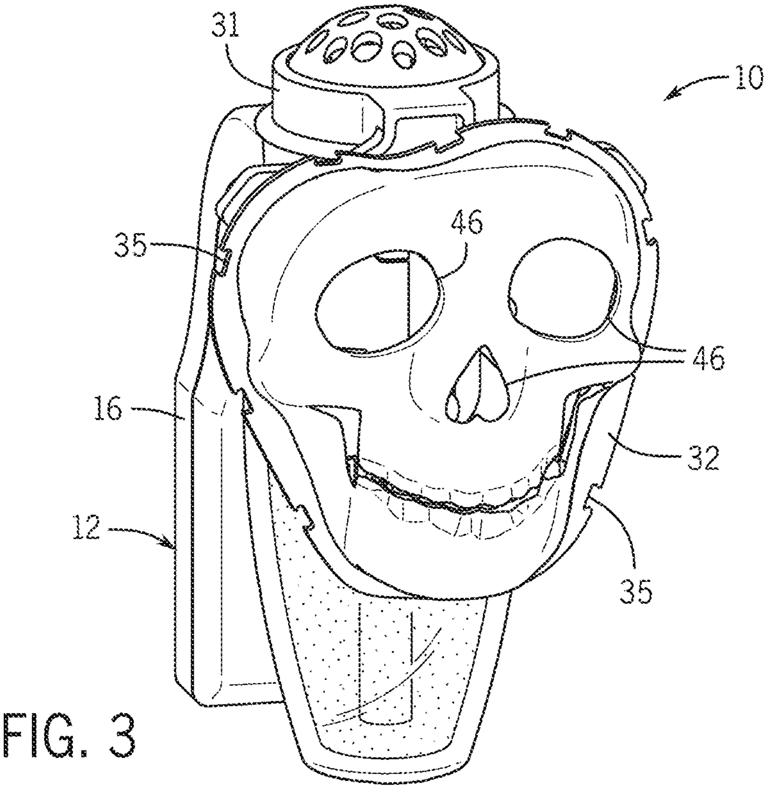
FIG. 3 is a front perspective view of the assembly of FIGS. 1 and 2, with an outer decorative element removed.

Before any embodiments of the invention are explained in detail, it is to be understood that unless expressly stated otherwise herein, the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless otherwise specified or limited, the phrases "at least one of A, B, and C," "one or more of A, B, and C," and the like, are meant to indicate A, or B, or C, or any combination of A, B, and/or C, including combinations with multiple instances of A, B, and/or C. Likewise, unless otherwise specified or limited, the terms "mounted," "connected," "linked," "supported," and "coupled" and variations thereof are used broadly and encompass both direct and indirect mountings, connections, supports, and couplings. Further, unless otherwise specified or limited, "connected" and "coupled" are not restricted to physical or mechanical connections or couplings.

As used herein, unless otherwise limited or defined, discussion of particular directions is provided by example only, with regard to particular embodiments or relevant illustrations. For example, discussion of "top," "bottom," "front," "back," "left," "right," "lateral" or "longitudinal" features is generally intended as a description only of the orientation of such features relative to a reference frame of a particular example or illustration. Correspondingly, for example, a "top" feature may sometimes be disposed below a "bottom" feature (and so on), in some arrangements or embodiments. Additionally, use of the words "first," "second", "third," etc. is not intended to connote priority or importance, but merely to distinguish one of several similar elements from another.

FIGS. 1-6 show a first example of an assembly 10 according to the present disclosure, which is in the form of a plug-in fragrance dispenser. The assembly 10 includes a base 12, which comprises a first housing portion 16 configured to support a printed circuit board (PCB) 18 that is electrically connected to a plug 20. The base 12 also includes a second housing portion 22 configured to hold a heater 24 that heats a wick 26 that extends from a bottle 28 filled with a fragrant liquid, all as is known. The second housing portion 22 supports a bracket 30 (FIG. 4) to which an inner decorative element 32 (FIG. 3) is attached, such as by way of a snap fit, adhesive, or other known fastening means. In the present example, the bracket 30 is supported by a support ring 31 that fits around a top end of the second housing portion 22. In the present example, the inner decorative element 32 is attached to the bracket 30 by way of two protrusions 33 on the rear-facing side of the inner decorative element 32 (see FIG. 5) that snap and/or are friction fit into slots 29 formed in the bracket 30 (see FIG. 4). An outer decorative element 14 (FIGS. 1 and 2) is in turn attached to the inner decorative element 32, again, such as by way of known fastening means. In the present example, tabs 15 on the outer perimeter of the outer decorative element 14 snap around and/or fit into slots 35 formed in the outer perimeter of the inner decorative element 32. The outer and inner decorative elements 14, 32 may have the same shape/design or may have different shapes/designs, but typically, at least some gap(s) is/are present between the surfaces of the outer and inner decorative elements that face one another. As can be seen from FIG. 1, the outer decorative element 14 is configured to at least partially hide the base 12 from view when the assembly 10 is viewed from a front side thereof.

Figure 4:
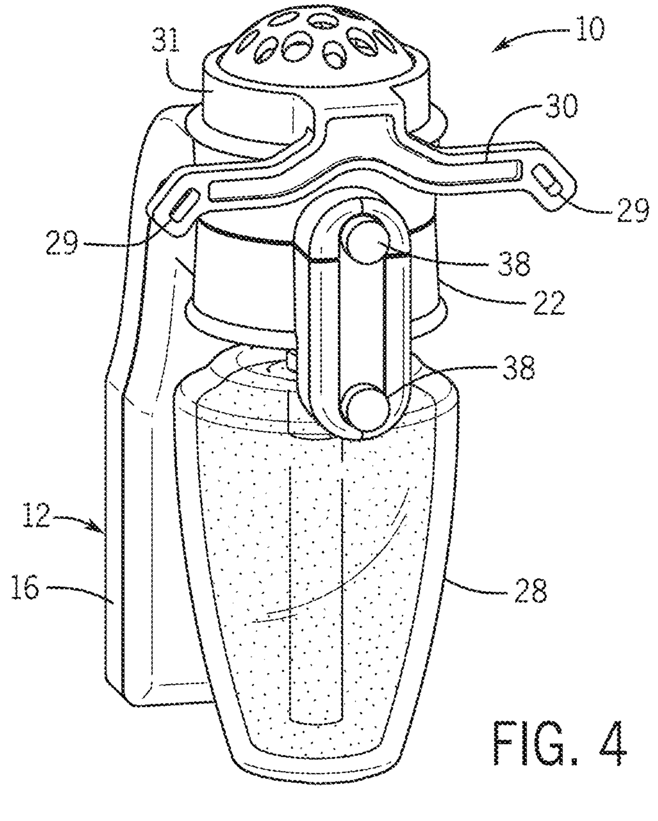
FIG. 4 is a front perspective view of the assembly of FIGS. 1-3, with outer and inner decorative elements removed.
Figure 5:
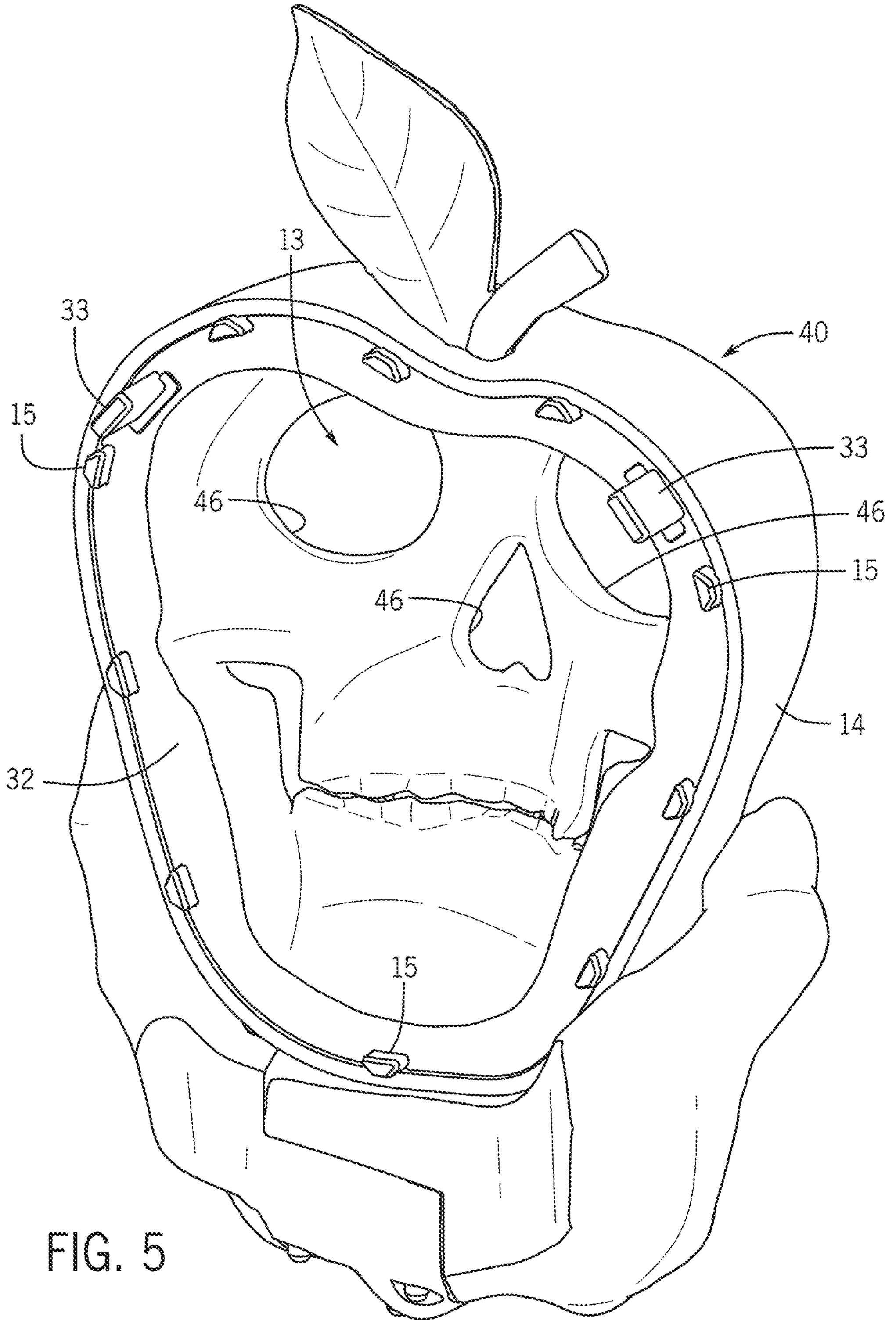
FIG. 5 is a rear perspective view of the inner and outer decorative elements in isolation.
Figure 6:
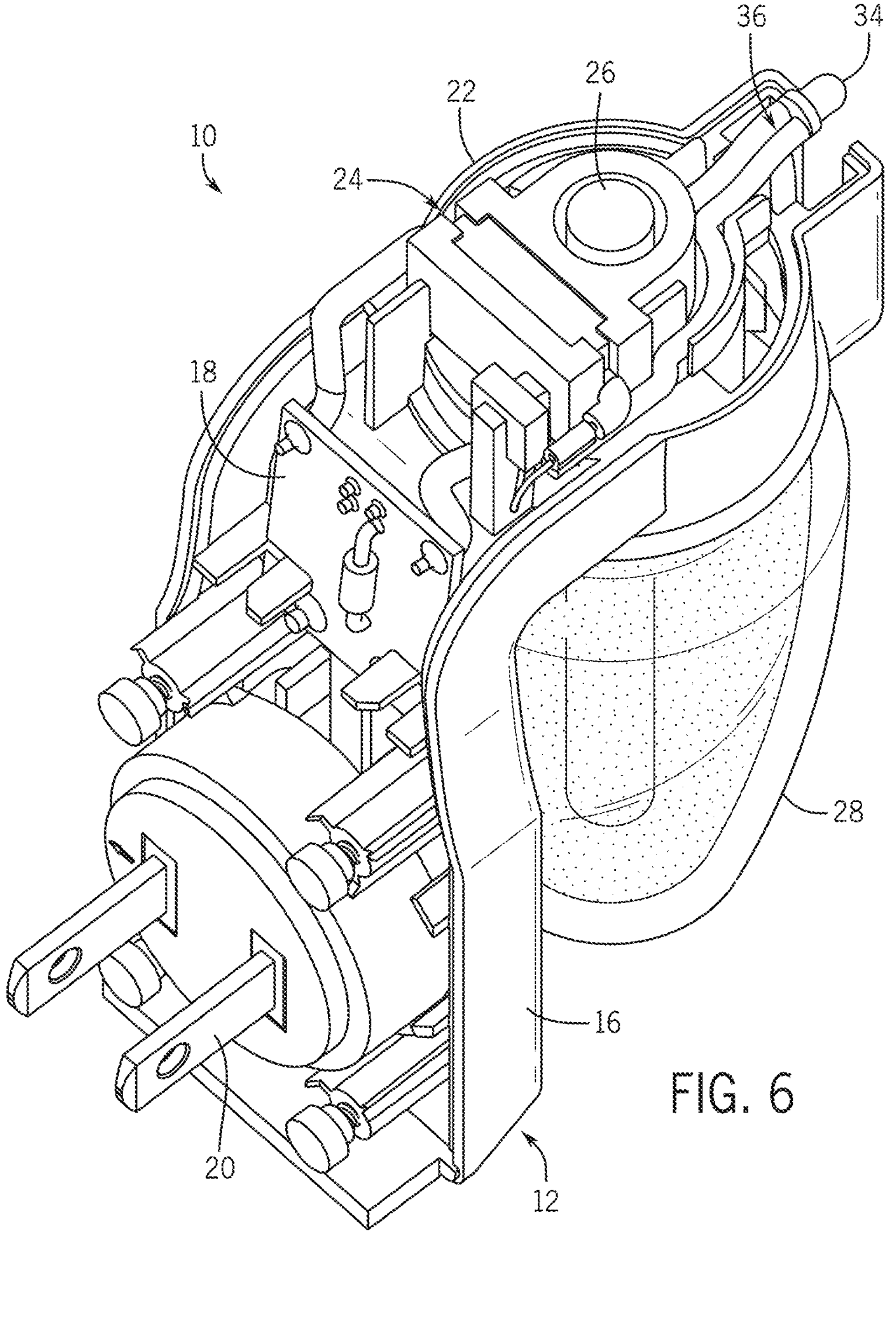
FIG. 6 is a rear perspective view of the assembly of FIGS. 1-4, showing additional components removed from the assembly.

The assembly 10 also includes a light source 34 (FIG. 6) configured to be selectively illuminated. For example, when the assembly 10 is plugged into an electrical outlet via the plug 20, and a switch on the PCB 18 is in a first state, current is provided to the light source 34 via wires 36 to thereby illuminate the light source 34. In the present example, the light source 34 is a light-emitting diode, but the light source could be another type of light source, such as an incandescent, halogen, or compact fluorescent light bulb. Although only one light source 34 is shown herein, two or more light sources may be provided. Each light source 34 is covered by a lens 38, two of which are shown in FIG. 4, each lens 38 being positioned in front of a respective light source. The lenses 38 are transparent or translucent covers coupled to the front end of the second housing portion 22. In other examples, no lenses are provided and the light source(s) 34 shine through uncovered apertures formed in the front end of the second housing portion 22.

Figure 7:
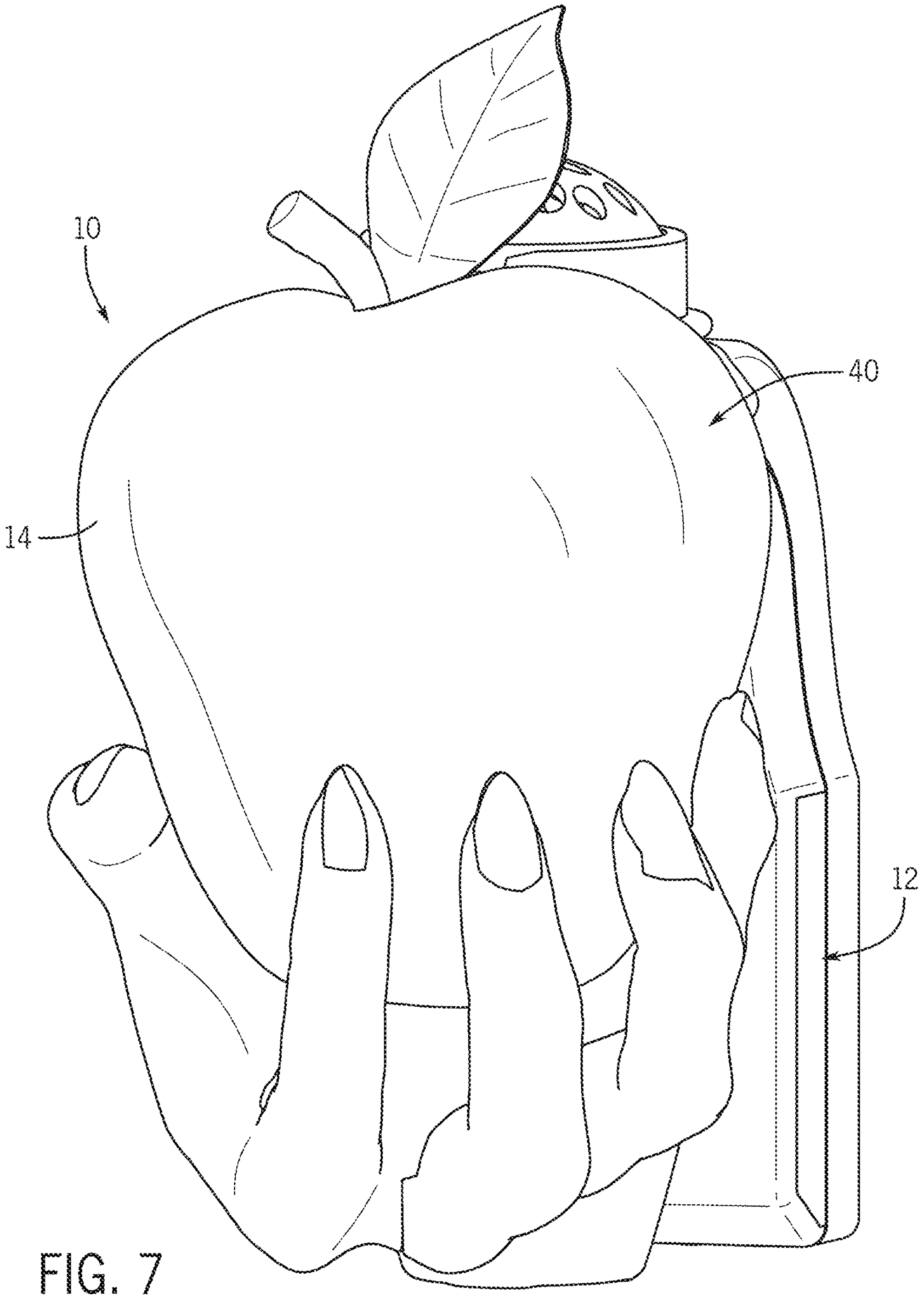
FIG. 7 shows the assembly of FIGS. 1-6 with a light source thereof in an unilluminated state.
Figure 8:
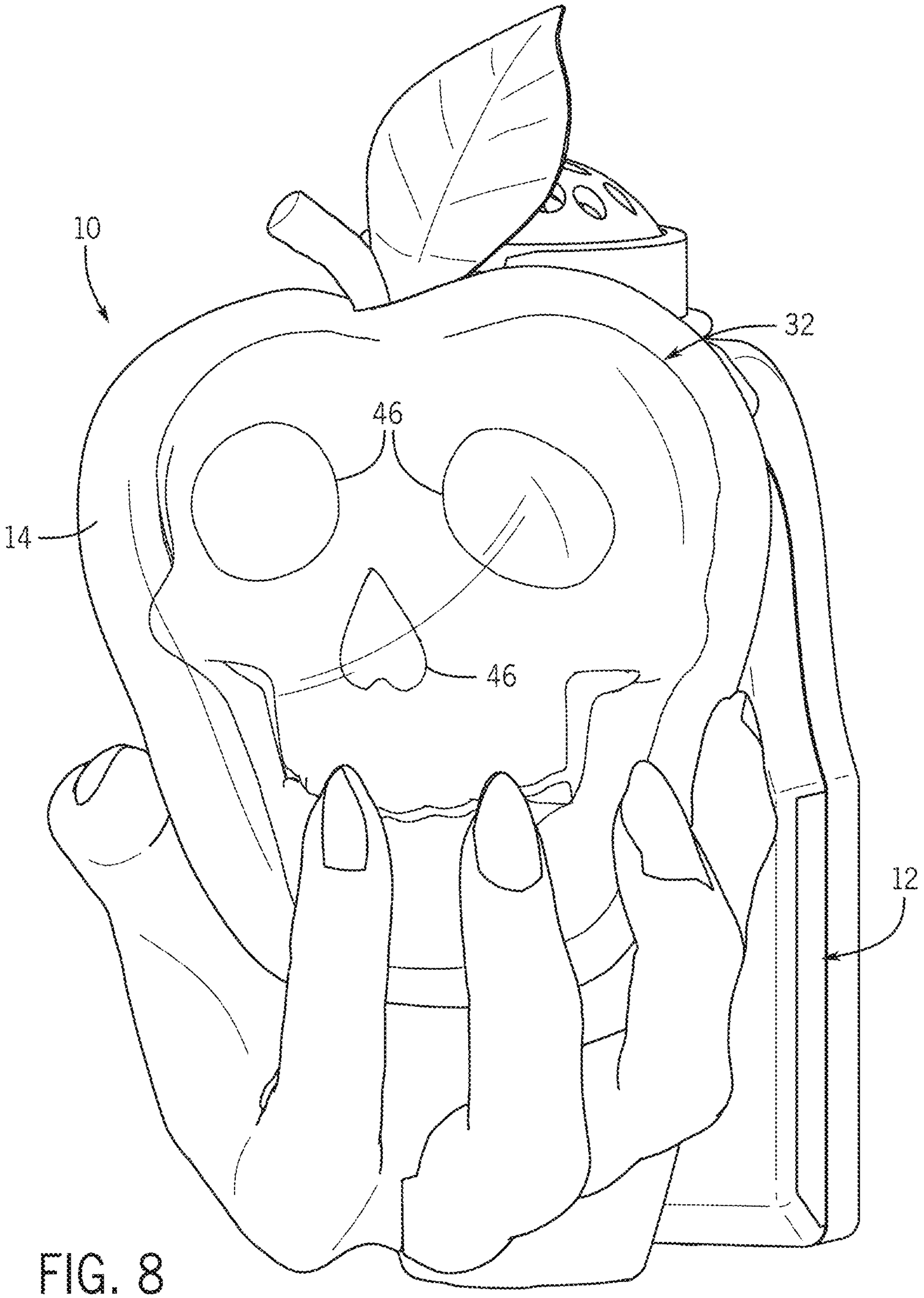
FIG. 8 shows the assembly of FIGS. 1-7 with the light source illuminated.

Thus, it can be seen that the inner decorative element 32 is located between the light source 34 and the outer decorative element 14. The outer decorative element 14 is specifically designed such that the inner decorative element 32 is not visible through the outer decorative element 14 when the light source 34 is not illuminated, but the inner decorative element 32 is visible through the outer decorative element 14 when the light source 34 is illuminated. For example, FIG. 7 shows the assembly 10 when the light source 34 is not illuminated. The inner decorative element 32 (the skull) is not visible through the outer decorative element 14 (the apple). FIG. 8, on the other hand, shows the assembly 10 when the light source 34 is illuminated. The inner decorative element 32 (the skull) is visible through the outer decorative element 14 (the apple).

In order to achieve this effect, the outer decorative element 14 comprises a transparent or translucent substrate that is coated with a metal coating. In one example, the transparent or translucent substrate is plastic, but the outer decorative element 14 could instead be made of glass. By referring to the substrate of the outer decorative element 14 as "transparent or translucent," it is understood that this describes the transparency or translucency of the substrate prior to it being coated with the metal coating-after being coated with the metal coating, the outer decorative element 14 is transparent or translucent only when the light source 34 is illuminated. The metal coating is applied to the substrate of the outer decorative element 14 with a thickness and density such that only a portion of the light that hits the surface of the outer decorative element 14 is reflected back. In essence, the outer decorative element 14 functions as a one-way mirror.

When the light source 34 is not illuminated, the metal-coated outer decorative element 14 appears to be opaque, but in fact, the metal coating is partially reflective and partially transparent. When the light source 34 is not illuminated, light from an external light source (e.g., ambient light) that shines on the outwardly facing surface 40 of the outer decorative element 14 is brighter than light shining on the opposite inwardly facing surface 13 (FIG. 5) of the outer decorative element 14 (i.e., the surface that faces the light source 34). There is not as much light on the inwardly facing surface 13 of the outer decorative element 14 because the inwardly facing surface 13 faces a wall when the assembly 10 is plugged into an outlet in the wall. When the light source 34 is not illuminated, the portion of light that does pass from the inwardly facing surface 13 to the outwardly facing surface 40 of the outer decorative element 14 is overwhelmed by the light reflected off the outwardly facing surface 40. Thus, when the light source 34 is not illuminated, the metal coating is reflective and is configured to reflect external light outwardly away from the outer decorative element 14.

In non-limiting examples, the thickness and density of the metal coating are such that the ratio of light intensity directed toward the inwardly facing surface 13 of the outer decorative element 14 to light intensity directed toward the outwardly facing surface 40 of the outer decorative element 14 needs to be at least 2:1 in order for the outer decorative element 14 to appear transparent. In other words, in such non-limiting examples, the light source 34 needs to be at least twice as bright as the ambient light before the outer decorative element 14 will appear transparent. When the light source 34 is illuminated, the portion of the relatively more intense light shining on the inwardly facing surface 13 of the outer decorative element 14 that shines through the metal coating is not overwhelmed by the ambient light, rendering the outer decorative element 14 transparent. The ratio of 2:1 mentioned herein is merely exemplary and different ratios could be used, such as 1.1:1, 1.2:1, 1.3:1, 1.4:1, 1.5:1, 1.6:1, 1.7:1, 1.8:1, 1.9:1, 2.1:1, 2.2:1, 2.3:1, 2.4:1, 2.5:1, etc. The thickness and/or density of the metal coating and the intensity of the light source can be specifically paired to ensure that the outer decorative element 14 is reflective under typical ambient conditions when the light source 34 is not illuminated, but is transparent or translucent when the light source 34 is illuminated.

The metal coating can be applied to the plastic or glass substrate of the outer decorative element 14 in any known manner, such as vacuum metalizing, electroless plating, electroplating, or spraying, with vacuum metalizing being preferred. The metal coating can be made of copper, nickel, silver, aluminum, or another metal or alloy known for being reflective and capable of being applied to glass or plastic via a metallization process. In non-limiting examples, the metal coating is on the order of 0.01 mm to 2.0 mm thick. However, the metal coating can be any appropriate thickness and density such that the outer decorative element 14 is translucent or transparent when the light source 34 is illuminated. The metal coating can be applied to the inwardly facing surface of the outer decorative element 14 or to the outwardly facing surface 40 thereof, and in one example is applied to the outwardly facing surface 40 of the outer decorative element 14 such that there is no barrier (e.g., the transparent or translucent substrate) between the metal coating and the reflected external light. In the present example, the metal coating is applied to the entirety of the outwardly facing surface 40 of the outer decorative element 14. In other examples, the metal coating could be applied only to portions of the substrate, such as in selected areas, decorative patterns, etc. The metal coating can have any color, which can be a single solid color or which could comprise multiple colors forming (by way of example only) a shape, image, speckled effect, or ombre effect.

The light source 34 preferably emits white light, although other colors of light could be used. The luminous intensity of the light source 34 is high enough to be brighter than a typical surrounding area in order to achieve the effect of rendering the outer decorative element 14 transparent or translucent when the light source 34 is illuminated. In one example, the illuminance level of the surrounding area (ambient light) is about 10 lux to 600 lux. The light source 34 can be directional or non-directional. Preferably, a lens 38 is provided between the light source 34 and the inner decorative element 32 in order to diffuse the light.

Figure 9:
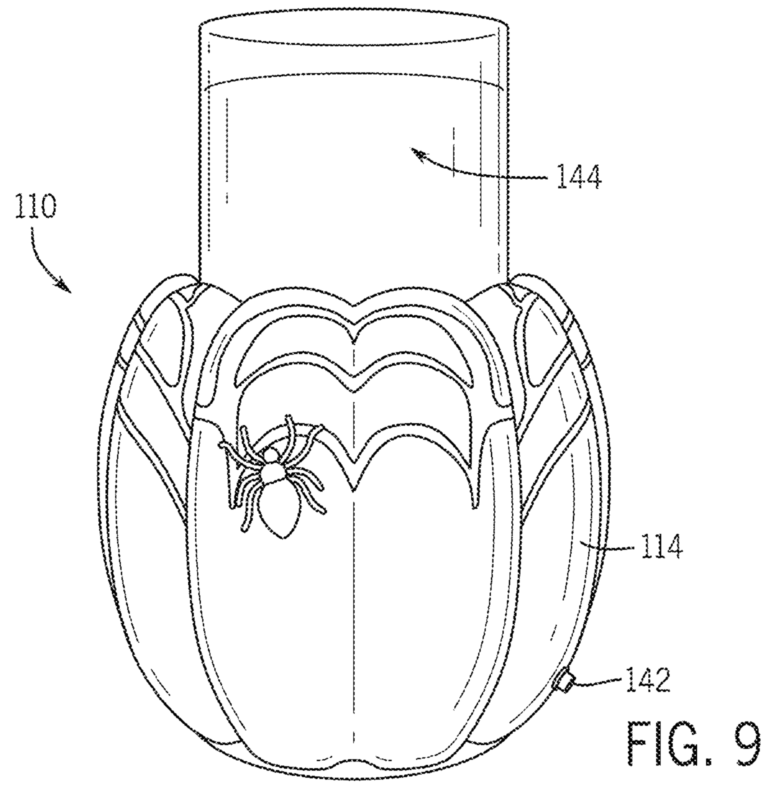
FIG. 9 is a front view of a second example of an assembly according to the present disclosure, with a light source thereof in an unilluminated state.
Figure 10:
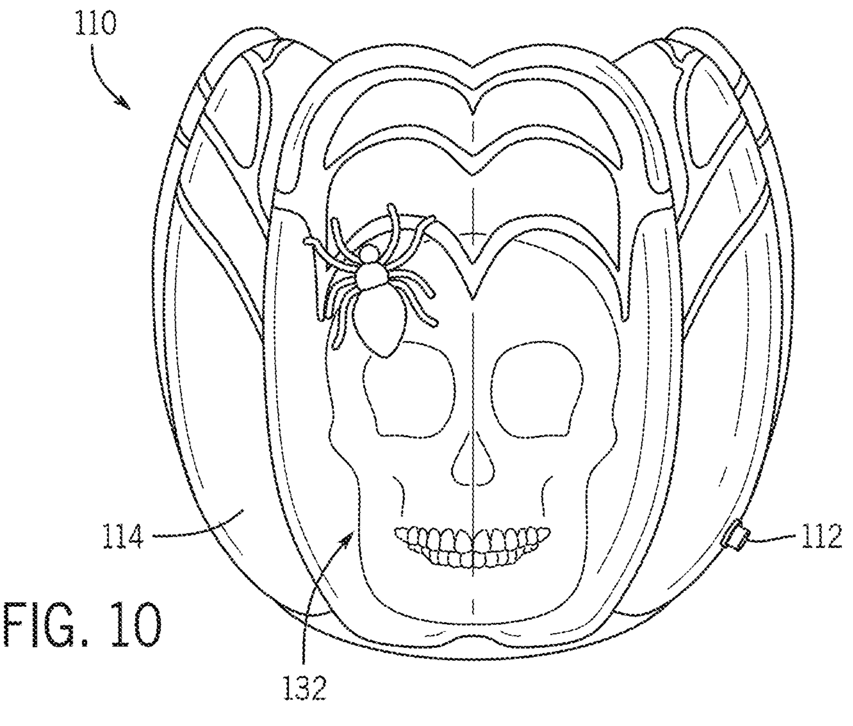
FIG. 10 shows the assembly of FIG. 9 with the light source illuminated.

As mentioned briefly above, the outer decorative element 14, the inner decorative element 32, and the light source 34 are coupled to a base 12. The base 12 is in turn configured to be coupled to a power source, such as via a plug 20. In another example, as shown in FIGS. 9 and 10, the power source is internal to the assembly 110. The assembly 110 in this example comprises a light source (not shown, but evident from FIG. 10) configured to be selectively illuminated; an outer decorative element 114; and an inner decorative element 132 between the light source and the outer decorative element 114. The outer decorative element 114 comprises a transparent or translucent substrate that is coated with a metal coating. The base 112 in this instance is the bottom of the outer decorative element 114, which is built as a platform to hold the inner decorative element 132 and a battery, the latter of which serves as the power source. A switch 142 is provided to connect the battery to the light source or disconnect the battery from the light source. The assembly 110 in this example is a candle holder configured to hold a candle 144. In other examples, the assembly may be a decorative item that performs no substantive functional purpose. Unless otherwise noted, the elements of the assembly 110 shown in FIGS. 8 and 9 function in the same or similar manner to those elements referenced by the same numbers in the one's and ten's place in the example of FIGS. 1-7 and will therefore not be described further herein.

As shown in FIG. 10, the inner decorative element 132 is translucent and the light emanating from the light source is visible through the material of the inner decorative element 132. This may allow both the inner decorative element 132 and the outer decorative element 114 to fully surround the light source 360 degrees on all sides, and optionally on the top of the light source, which obscures elements such as the battery and any electrical connections within the surrounds of the inner decorative element 132.

In another example, as shown in FIG. 8, the inner decorative element 32 is opaque and comprises one or more apertures 46 therein. Here, the apertures 46 form the eyes and nose of the skull, but other shapes could be used. Light from the light source 34 can shine through the apertures 46 and provide contrasting effects insofar as what appears lighter or darker on the inner decorative element 32 when the light source 34 is illuminated. The apertures 46 also provide a pathway for light from the light source 34 to illuminate the inwardly facing surface of the outer decorative element 14 more than the outwardly facing surface thereof, thereby rendering the outer decorative element 14 translucent.

In still other examples, the inner decorative element 32, 132 may be translucent and may comprise apertures therein. In still other examples, the inner decorative element 32, 132 may be opaque and may have no apertures, but may have a perimeter that is smaller than that of the outer decorative element 14, 114 such that light from the light source can shine around the outer perimeter of the inner decorative element 32, 132 to illuminate the inwardly facing surface of the outer decorative element 14, 114 and thereby render the outer decorative element 14, 114 translucent.

Although only a plug-in fragrance dispenser and a candle holder are shown herein, those having ordinary skill in the relevant art would understand how the components described hereinabove could be assembled into another type of home accessory.

In the above description, certain terms have been used for brevity, clarity, and understanding. No unnecessary limitations are to be inferred therefrom beyond the requirement of the prior art because such terms are used for descriptive purposes and are intended to be broadly construed. The order of method steps or decisions shown in the Figures and described herein are not limiting on the appended claims unless logic would dictate otherwise. It should be understood that the decisions and steps can be undertaken in any logical order and/or simultaneously. The different systems and methods described herein may be used alone or in combination with other systems and methods. It is to be expected that various equivalents, alternatives and modifications are possible within the scope of the appended claims.

What is claimed is:

1. An assembly comprising:

a light source configured to be selectively illuminated;

an outer decorative element having an inwardly facing surface that faces toward the light source; and an inner decorative element between the light source and the outer decorative element, the inner decorative element having an outwardly facing surface that faces away from the light source;

wherein the inner decorative element and the outer decorative element are separate and distinct components, and an air gap is present between the outwardly facing surface of the inner decorative element and the inwardly facing surface of the outer decorative element; and wherein the outer decorative element comprises a transparent or translucent substrate and an entirety of the transparent or translucent substrate is coated with a metal coating.

2. The assembly of claim 1, wherein the metal coating is reflective.

3. The assembly of claim 2, wherein the metal coating is configured to reflect external light outwardly away from the outer decorative element.

4. The assembly of claim 1, wherein the inner decorative element is not visible through the outer decorative element when the light source is not illuminated.

5. The assembly of claim 1, wherein the inner decorative element is visible through the outer decorative element when the light source is illuminated.

6. The assembly of claim 1, wherein the inner decorative element is not visible through the outer decorative element when the light source is not illuminated; and wherein the inner decorative element is visible through the outer decorative element when the light source is illuminated.

7. The assembly of claim 1, wherein the outer decorative element, the inner decorative element, and the light source are coupled to a base that is in turn configured to be coupled to a power source; and wherein the light source is configured to be electrically connected to the power source so as to illuminate the light source.

8. The assembly of claim 1, wherein the assembly is a plug-in fragrance dispenser.

9. The assembly of claim 8, further comprising:

a base configured to support the outer decorative element, the inner decorative element, and the light source;

a plug coupled to the base and configured to connect the light source to a power source to selectively illuminate the light source; and a heater supported by the base and configured to emit heat when selectively connected to the power source via the plug;

wherein the base is configured to hold a bottle comprising a fragrant liquid therein in a manner such that a wick extending from the bottle is located adjacent the heater; and wherein the outer decorative element is configured to at least partially hide the base from view when the assembly is viewed from a front side thereof.

10. The assembly of claim 1, wherein the assembly is a candle holder.

11. The assembly of claim 1, wherein the transparent or translucent substrate is plastic.

12. The assembly of claim 1, wherein the inner decorative element is translucent.

13. The assembly of claim 1, wherein the inner decorative element is opaque and comprises one or more apertures therein.

14. An assembly comprising:

a light source configured to be selectively illuminated;

an outer decorative element having an inwardly facing surface that faces toward the light source; and an inner decorative element between the light source and the outer decorative element, the inner decorative element having an outwardly facing surface that faces away from the light source;

wherein the inner decorative element and the outer decorative element are separate and distinct components, and an air gap is present between the outwardly facing surface of the inner decorative element and the inwardly facing surface of the outer decorative element;

wherein the inner decorative element is not visible through the outer decorative element when the light source is not illuminated; and wherein the inner decorative element is visible through the outer decorative element when the light source is illuminated.

15. The assembly of claim 14, wherein the outer decorative element comprises a transparent or translucent substrate and an entirety of the transparent or translucent substrate is coated with a metal coating.

16. The assembly of claim 15, wherein the metal coating is reflective.

17. The assembly of claim 16, wherein the metal coating is configured to reflect external light outwardly away from the outer decorative element.

18. The assembly of claim 14, wherein the outer decorative element, the inner decorative element, and the light source are coupled to a base that is in turn configured to be coupled to a power source; and wherein the light source is configured to be electrically connected to the power source so as to illuminate the light source.

19. The assembly of claim 14, wherein the assembly is a plug-in fragrance dispenser.

20. The assembly of claim 19, further comprising:

a base configured to support the outer decorative element, the inner decorative element, and the light source;

a plug coupled to the base and configured to connect the light source to a power source to selectively illuminate the light source; and a heater supported by the base and configured to emit heat when selectively connected to the power source via the plug;

wherein the base is configured to hold a bottle comprising a fragrant liquid therein in a manner such that a wick extending from the bottle is located adjacent the heater; and wherein the outer decorative element is configured to at least partially hide the base from view when the assembly is viewed from a front side thereof.

* * * * *